(12) United States Patent
He et al.

(10) Patent No.: US 12,415,800 B2
(45) Date of Patent: Sep. 16, 2025

(54) PREPARATION METHOD FOR LOSARTAN

(71) Applicant: Zhejiang Tianyu Pharmaceutical Co., Ltd., Zhejiang (CN)

(72) Inventors: Zuwei He, Zhejiang (CN); Gang Liu, Zhejiang (CN); Dequan Su, Zhejiang (CN); Ruiyun Lv, Zhejiang (CN); Wei Xiao, Zhejiang (CN); Zhen Wang, Zhejiang (CN); Guorong Zhu, Zhejiang (CN); Yongjun Tu, Zhejiang (CN)

(73) Assignee: Zhejiang Tianyu Pharmaceutical Co., Ltd. (CN)

( * ) Notice: Subject to any disclaimer, the term of this patent is extended or adjusted under 35 U.S.C. 154(b) by 907 days.

(21) Appl. No.: 17/629,990

(22) PCT Filed: Jan. 17, 2020

(86) PCT No.: PCT/CN2020/072571
§ 371 (c)(1),
(2) Date: Jan. 25, 2022

(87) PCT Pub. No.: WO2021/036193
PCT Pub. Date: Mar. 4, 2021

(65) Prior Publication Data
US 2022/0388988 A1 Dec. 8, 2022

(30) Foreign Application Priority Data
Aug. 29, 2019 (CN) .......................... 201910810615.3

(51) Int. Cl.
C07D 403/10 (2006.01)

(52) U.S. Cl.
CPC ................................. C07D 403/10 (2013.01)

(58) Field of Classification Search
CPC .................................................... C07D 403/10
See application file for complete search history.

(56) References Cited

U.S. PATENT DOCUMENTS

| 7,868,180 B2 * | 1/2011 | Veverka | ............... | C07D 233/68 548/262.2 |
| 2009/0203920 A1 | 8/2009 | Welzig et al. | | |

FOREIGN PATENT DOCUMENTS

| CN | 101253131 A | 8/2008 |
| CN | 101402630 A | 4/2009 |
| CN | 106749065 A | 5/2017 |
| CN | 107056756 A | 8/2017 |
| CN | 107573388 A | 1/2018 |
| CN | 109748905 A | 5/2019 |

OTHER PUBLICATIONS

Chinese Search Report for Application No. 201910810615.3 dated Mar. 18, 2020, 2 pages.

(Continued)

Primary Examiner — Golam M Shameem
(74) Attorney, Agent, or Firm — Lerner David LLP

(57) ABSTRACT

Provided is a preparation method of losartan, which is prepared by reacting a cyano group-containing intermediate represented by formula (I) with an azide reagent in toluene in the presence of a catalyst; wherein, after the reaction is completed, azide ions are removed by means of the following process: adding water to divide the reaction system into three layers, separating the intermediate layer and adding n-butanol to the intermediate layer for dilution, and adding triphenylphosphine to the resulting diluted solution so as to remove residual azide ions from the diluted solution. The preparation method provided by the present invention does not need to use sodium nitrite, thus fundamentally eliminating the formation of genotoxic impurities nitrosamines. The resulting target product has good purity, high yield, a simple preparation process, mild and easy-to-control operating conditions, and good safety, and is suitable for large-scale industrial production,

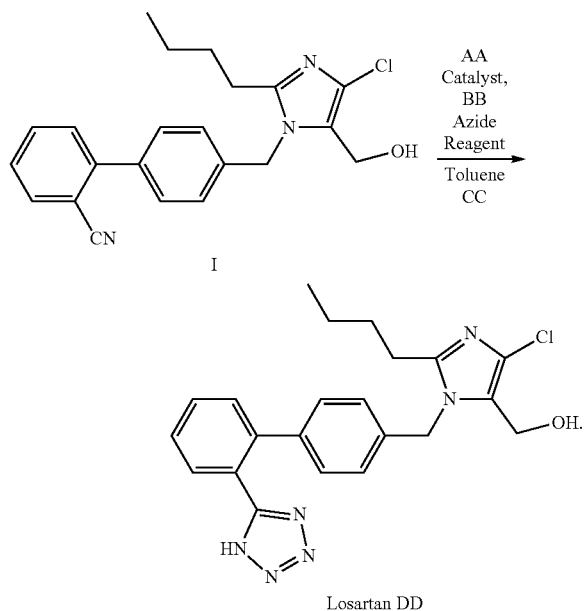

AA CATALYST
BB AZIDE REAGENT
CC TOLUENE
DD LOSARTAN

20 Claims, 1 Drawing Sheet

(56) References Cited

OTHER PUBLICATIONS

International Search Report for Application No. PCT/CN2020/072571 mailed Feb. 26, 2020, 2 Pages.

Zhao Tingxing, "Synthesis of Several Abbreviated Energetic Derivatives," Master's Degree Thesis of Southwest University of Science and Technology, Feb. 2016, pp. 21-23.

* cited by examiner

PREPARATION METHOD FOR LOSARTAN

CROSS-REFERENCE TO RELATED APPLICATION

This application is a U.S. national stage application, filed under 35 U.S.C. § 371, of International Patent Application No. PCT/CN2020/072571, filed on Jan. 17, 2020, which claims priority from Chinese Application No. 201910810615.3, filed Aug. 29, 2019, all of which is incorporated by reference herein in its entirety.

TECHNICAL FIELD

The present invention relates to the field of preparing pharmaceutical intermediates, in particular to a preparation method of losartan.

BACKGROUND

Losartan potassium is a commonly used antihypertensive drug of the type of angiotensin II receptor 1 antagonist (ARB). The chemical name of losartan potassium is 5-(4'-((2-butyl-4-chloro-5-(hydroxymethyl)-1H-imidazol-1-yl) methyl)-[1,1'-biphenyl]-2-yl) tetrazol-1-ide potassium, CAS: 124750-99-8, and the chemical structure of losartan potassium is as follows:

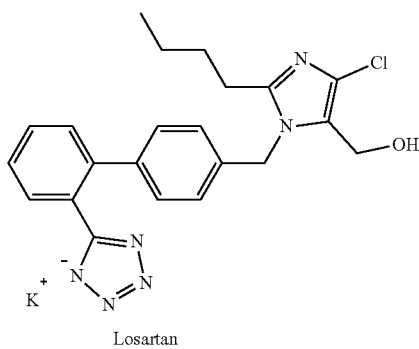 [SMILES: CCCCc1nc(Cl)c(CO)n1Cc1ccc(-c2ccccc2-c2nnn[n-]2)cc1 ; [K+]]

Losartan

Losartan is an important intermediate for the synthesis of losartan potassium. In the prior art, the synthesis method of losartan is shown in FIG. 1. In the existing process, such as the synthesis method of losartan disclosed in patents such as IN1524/MUM/2011A, dimethylformamide (DMF) is used as solvent to synthesize a cyanobiphenyl intermediate 3, and then the corresponding cyanobiphenyl intermediate 3 (containing DMF residue) and sodium azide ($NaN_3$) are added to n-methyl pyrrolidone (NMP) solvent, and losartan 4 is obtained by constructing tetrazole through cycloaddition reaction under the catalysis of triethylamine hydrochloride (TEA HCl). After the reaction is completed, excessive sodium azide was quenched by sodium nitrite in a water layer containing losartan. The quenching system contains trace amounts of secondary amines such as dimethylamine, diethylamine and 4-methylaminobutyric acid, and a nitrosation reaction of secondary amines is inevitably occurred, respectively forming genotoxic impurities nitrosamines such as dimethylnitrosamine (NDMA), diethylnitrosamine (NDEA) and 4-(methyl(nitroso)amino)butyric acid (NMBA), which may be brought into bulk drugs of losartan potassium.

Chinese patent CN 109748905A discloses an improved method for quenching azide, which needs to perform quenching by hydrogen peroxide in a water layer containing losartan. The quenching system reacts violently, producing a large number of bubbles, and the quenching process is difficult to control, and there may be potential safety hazards such as explosion of flushing materials during the scale-up production. In addition, hydrogen peroxide may also oxidize hydroxyl functional groups in losartan structure in the quenching system, resulting in oxidized impurities of losartan.

Thus, it can be seen that in the current production process of losartan, the process of quenching azide in the feed liquid containing the losartan product is required, and the risk of contamination by impurities cannot be completely eliminated under mild production conditions. Therefore, there is an urgent need to develop a preparation method of losartan that is suitable for industrial production and does not introduce toxic impurities.

SUMMARY

In order to overcome the above defects in the existing losartan production process, the object of the present invention is to provide is a preparation method of losartan.

The preparation method of losartan provided by the present invention is prepared by reacting a cyano group-containing intermediate represented by formula (I) with an azide reagent in toluene in the presence of a catalyst; wherein, after the reaction is completed, azide ions are removed by means of the following process: adding water to divide the reaction system into three layers, separating the intermediate layer and adding n-butanol to the intermediate layer for dilution, and adding triphenylphosphine to the resulting diluted solution so as to remove residual azide ions from the diluted solution,

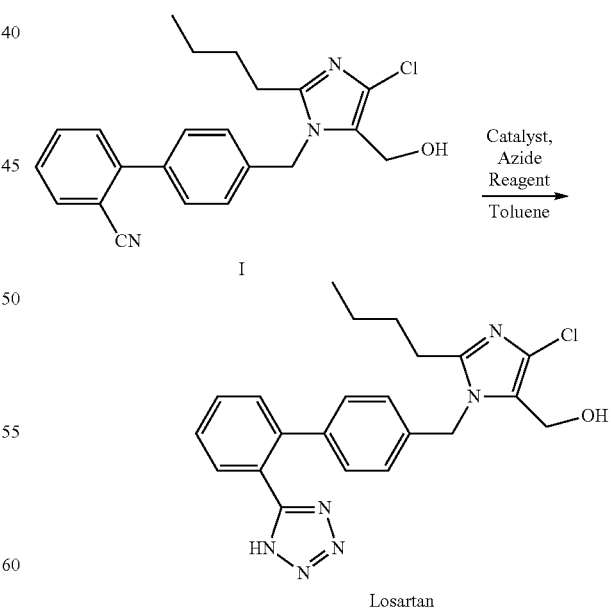

Losartan

In the preparation method of the present invention, after the reaction is completed, water is added first instead of directly quenching azide, so that the obtained reaction system can be obviously divided into three layers, i.e., an upper toluene layer, an intermediate oily product layer and a lower water layer, wherein most inorganic substances such as azide ions and catalysts exist in the water layer. Most azide ions can be removed by separating out the intermediate layer, while the diluted intermediate product layer contains only trace amount of azide ions, which can be completely removed by adding trace amount of triphenylphosphine to react with the azide ions.

In some embodiments, the water is added in an amount that is 0.8 times to 1.2 times that of the toluene by volume.

In some embodiments, the triphenylphosphine is added in an amount that is 2% to 10% of the cyano goup-containing intermediate by mole percentage. In some preferred embodiments, the triphenylphosphine is added in an amount that is 5% of the cyano group-containing intermediate by mole percentage.

In some embodiments, the preparation method further comprises adding triphenylphosphine into the diluted solution and simultaneously adding activated carbon for decolorization. The amount of the activated carbon that is added, decolorization time, decolorization temperature, or the like, can be determined by those skilled in the art according to the situation of the feed liquid. In some preferred embodiments, the activated carbon is added in an amount that can be 1.5 times to 3 times that of the triphenylphosphine by mass.

In some embodiments, the preparation method, after the azide ions are removed, further comprises the following process: evaporating the resulting diluted solution to dryness, adding an alkaline solution for saponification reaction, washing off impurities with toluene, adding a dispersing solvent and adding an acidic solution for acidification, and precipitating crystals to obtain the losartan. Residual impurities such as triphenylphosphine and azide ion reduzates can be removed by the step of toluene washing and the step of crystallization to further improve the product purity. Impurities related to triphenylphosphine are not detected in the resulting losartan product. In some preferred embodiments, when the toluene is used to wash off impurities, the washing times can be 1 times to 3 times.

In some embodiments, the alkaline solution for saponification reaction and the acidic solution for acidification can be solutions used in the conventional preparation process of losartan. In some preferred embodiments, the alkaline solution can be sodium hydroxide or potassium hydroxide solution with a mass percentage of 1% to 5%, and the amount of the alkaline solution added can be 5 times to 10 times that of the cyano group-containing intermediate by mass. In another preferred embodiments, the acidic solution can be hydrochloric acid or sulfuric acid solution with a volume percentage of 5% to 10%, and is acidified to a pH value of 3 to 4.

In some embodiments, the dispersing solvent can be a solvent used in the conventional preparation process of losartan. In some preferred embodiments, the dispersing solvent can be dichloromethane, and the amount of the dispersing solvent added can be 0.3 times to 0.8 times that of the alkaline solution by volume.

In the preparation method provided by the present invention, the azide reagent can be an azide reagent used in the conventional preparation process of losartan, comprising but not limited to sodium azide, potassium azide, lithium azide and the like. In some preferred embodiments, the azide reagent can be sodium azide.

In some embodiments, the catalyst can be triethylamine hydrochloride.

In some embodiments, a molar ratio of the cyano group-containing intermediate: the azide reagent:the catalyst can be 1:2.5-3.5:2.0-3.0. In some preferred embodiments, the molar ratio of the cyano group-containing intermediate:the azide reagent:the catalyst can be 1:3.0:2.5.

In some embodiments, a mass ratio of the cyano group-containing intermediate to the toluene can be 1: 1-5. In some preferred embodiments, the mass ratio of the cyano intermediate to the toluene can be 1:2.

In some embodiments, a temperature range of the reaction between the cyano group-containing intermediate and the azide reagent can be 90° C.-95° C.

In the preparation method provided by the present invention, the cyano group-containing intermediate shown in formula (I) can come from any source, for example, purchased commercially or synthesized with reference to literatures.

In some embodiments, as shown in FIG. 2, the cyano group-containing intermediate used in the present invention can be prepared by the following process:

dissolving compound 1 in toluene and condensing compound 1 with aldehyde 2 in the presence of tetraethyl ammonium bromide; after the reaction was completed, directly reducing the resulting compound 3 by sodium borohydride without purifying and separating compound 3, and crystallizing the resulting product in a mixed solvent of toluene and diethylacetamide to obtain compound 4 (i.e., the cyano group-containing intermediate).

In some preferred embodiments, a mass ratio of the compound 1 to tetraethyl ammonium bromide can be 1:0.02-0.15, and preferably 1:0.08.

In some preferred embodiments, a weight ratio of the toluene to the diethylacetamide used for crystallization can be 60:1.

The preparation method of losartan provided by the present invention has the following advantages.

(1) There is no need to use sodium nitrite to quench azide ions in the presence of a product, thus fundamentally eliminating the formation of genotoxic impurities nitrosamines. The residual trace amount of azide ions can be removed by using trace amount of triphenylphosphine, with good removal effect, less reagent consumption and new impurities are not be introduced.

(2) The resulting losartan product has good purity and high yield.

(3) The preparation process is simple with mild and easy-to-control operating conditions, and good safety, and is suitable for large-scale industrial production.

EMBODIMENTS

Figure 1:
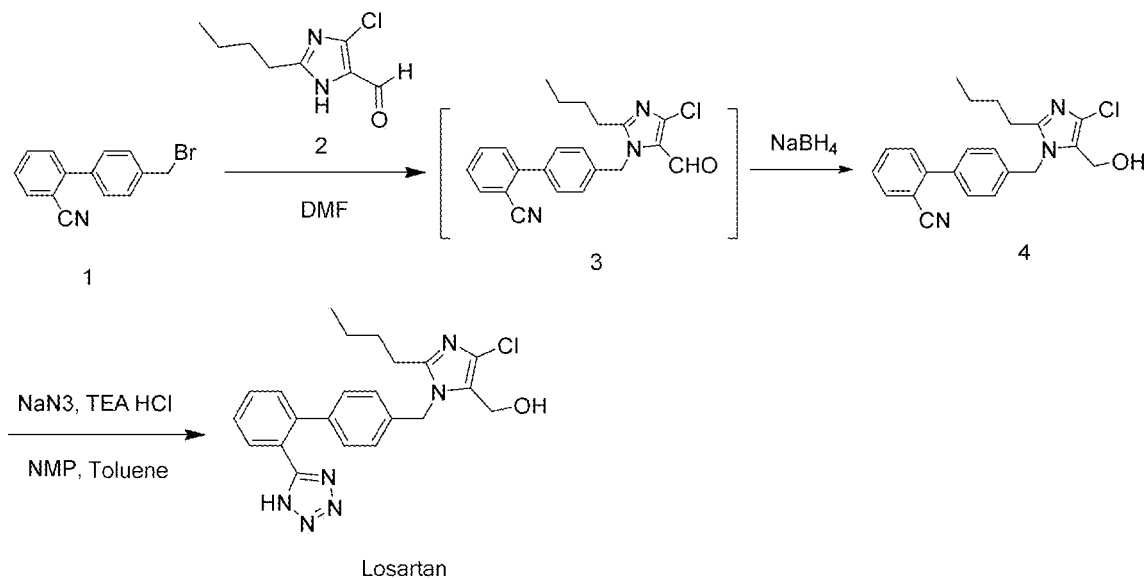
FIG. 1 is a synthesis route of losartan in the prior art.
Figure 2:
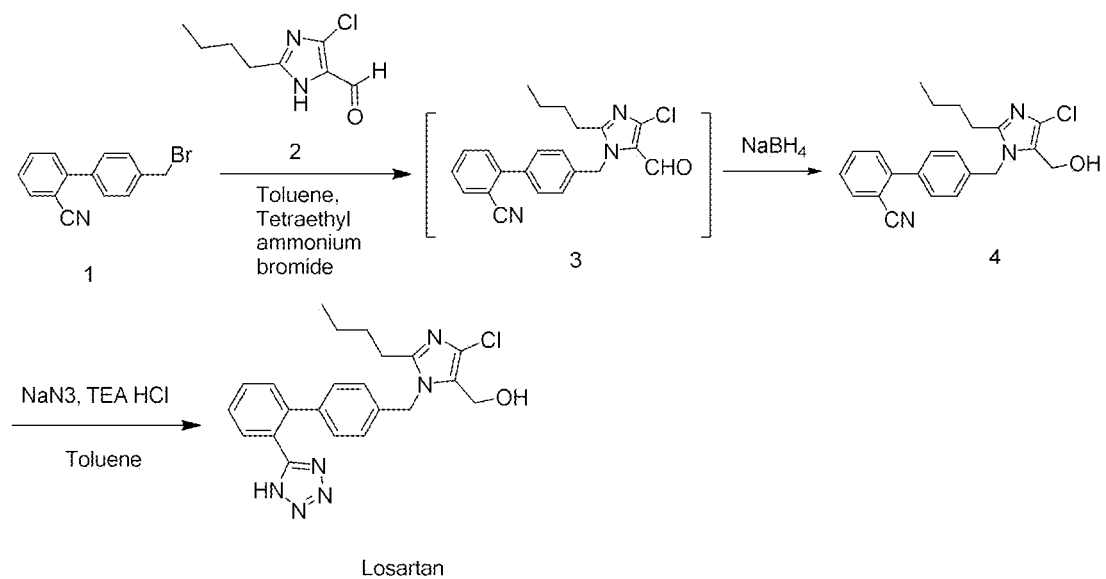
FIG. 2 is a synthesis route of losartan used in the present invention.

The technical solutions of the present invention will be further described in detail below with reference to the specific embodiments.

Device information and service conditions of an ion chromatograph (HPIC) used in the embodiments of the present invention are as follows:

(1) Device information
Instrument: DIONEX ICS900 ion chromatograph equipped with electrical conductivity detector;
Chromatographic column: Ionpac AS18 4.0×250 mm;
Detector: electrical conductivity detector; and Chromatography workstation: DIONEX chameleon chromatography workstation.

(2) Chromatographic analysis conditions

Washing agent: KOH washing agent generator, and ultra-pure water;

Flow rate: 1.0 mL/min;

Column temperature: room temperature;

Injection volume: 200 μL;

Running time: 45 minutes; and

Gradient running schedule:

| Time, minute | Concentration of washing agent | Type of elution |
| --- | --- | --- |
| 0 to 25 | 9 mmol/L KOH | Balanced |
| 25 to 35 | 40 mmol/L KOH | Linear gradient |
| 35 to 45 | 9 mmol/L KOH | Rebalanced |

The main raw materials used in the embodiments of the present invention are as follows:

| Name of raw material | Specification/Grade | Manufacturer |
| --- | --- | --- |
| Compound 1 | Analytically pure | Tianyu Pharmaceutical Co., Ltd. |
| Compound 2 | Analytically pure | Tianyu Pharmaceutical Co., Ltd. |
| Tetraethyl ammonium bromide | Analytically pure | Aladdin Reagent Corporation |
| Toluene | Analytically pure | Sinopharm Chemical Reagent Co., Ltd. |
| N-butanol | Analytically pure | Sinopharm Chemical Reagent Co., Ltd. |
| Sodium borohydride | Analytically pure | Sinopharm Chemical Reagent Co., Ltd. |
| Triphenylphosphine | Analytically pure | Sinopharm Chemical Reagent Co., Ltd. |
| Diethylacetamide | Analytically pure | Aladdin Reagent Corporation |
| Triethylamine hydrochloride | Analytically pure | Aladdin Reagent Corporation |
| Sodium azide | Analytically pure | Aladdin Reagent Corporation |

In the embodiments of the present invention, other reagents used are all commercially available products unless otherwise specified, and the devices or operating methods used are all common devices or operating methods in the art unless otherwise specified.

Preparation Examples Preparation of Compound 4

365 g of toluene was added into a reaction flask, added with 56 g of compound 1, 33.6 g of sodium carbonate and 5.6 g of tetraethyl ammonium bromide under slow stirring, then the stirring was speeded up and the temperature was raised to 90° C.-95° C. The temperature was controlled at 90° C.-95° C., 142 g of toluene solution of 39.2 g of compound 2 was added dropwise for 3-4 hours. After the dropwise addition was completed, the temperature was kept for reaction for 4-5 hours. After the reaction was completed, 140 g of water was added and layered. Then, 1 g of tetraethyl ammonium bromide was added to the toluene layer, and the temperature was controlled at 20° C.-25° C. A pre-prepared mixed solution of sodium borohydride and sodium hydroxide (9 g of sodium borohydride, 5.6 g of sodium hydroxide and 24.5 g of water) was added dropwise. After the dropwise addition was completed, the temperature was kept at 20° C.-25° C. for 4 hours, and then the temperature was raised to 80° C.-85° C. and kept for reaction. After the reaction was completed, 105 g of water was added, and then the temperature was controlled at 80° C.-85° C. The temperature was kept for stirring for 10 minutes. Then, the reaction system was transferred to a separating funnel for standing and layering, and the water layer was discarded. The organic layer was transferred to a four-necked flask, added with 8.4 g of diethylacetamide and stirred. Then, the temperature was raised to 85° C.-90° C., and kept for crystallization. After the crystallization was completed, the temperature was reduced to 0° C.-5° C. and the crystals were filtered and dried in vacuum at 60° C. for 5-6 hours to obtain 71.9 g of compound 4 with a yield of 92%.

Example 1 Preparation of Losartan 40 g of toluene was added into a four-necked flask, added with 20 g of compound 4, 10.3 g of sodium azide and 18 g of triethylamine hydrochloride under slow stirring. After feeding, the temperature was raised to 90° C.-95° C., and kept for 35 hours-45 hours. After the reaction was completed, 40 g of water was added, and the temperature was reduced to 60° C.-70° C. The reaction system was stood for layering to separate the intermediate layer liquid, added with 40 ml of n-butanol for dissolution, washed twice with 20 g of saturated sodium chloride aqueous solution, added with 0.4 g of triphenylphosphine and 0.8 g of activated carbon, stirred, warmed up to 50° C.-60° C., and de-colored for 2 hours. The reaction system was subjected to hot filtering, and then the filter cake was washed with 10 ml of n-butanol, and the filtrates were combined. The temperature was controlled at 50° C.-80° C. The filter cake was dried under reduced pressure at a degree of vacuum over 0.08 MPa, and the dried product was added with 7.7 g of liquid alkali (concentrated sodium hydroxide solution with a mass concentration of about 50%) and 160 g of water, stirred and dissolved, 10 g of toluene was added to the water layer for extraction twice, 80 ml of dichloromethane was added to the water layer, the layer was cooled to 10° C.-15° C., and 7.5% hydrochloric acid (volume concentration) was added dropwise to adjust the pH to 3-4, the system was kept at 10° C.-15° C. for 1 hour, then cooled to 0° C.-5° C. and kept for 1 hour. The reaction system was filtered, and the filter cake was washed with 20 ml of dichloromethane and 40 g of water respectively, and dried under reduced pressure to obtain 20.2 g of losartan with a yield of 91%. Azide ions (HPIC detection) were not detected (detection limit: 0.081 ppm).

Example 2 Preparation of Losartan 40 g of toluene was added into a four-necked flask, added with 20 g of compound 4, 10.3 g of sodium azide and 18 g of triethylamine hydrochloride under slow stirring. After feeding, the temperature was raised to 90° C.-95° C., and kept for 35 hours-45 hours. After the reaction was completed, 40 g of water was added, and the temperature was reduced to 60° C.-70° C. The reaction system was stood for layering to separate the intermediate layer liquid, 40 ml of n-butanol was added for dissolution, the layer was washed twice with 20 g of saturated sodium chloride aqueous solution, 1.0 g of triphenylphosphine and 0.8 g of activated carbon were added, the system was stirred, warmed up to 50° C.-60° C., and de-colored for 2 hours. The reaction system was subjected to hot filtering, and then the filter cake was washed with 10 ml of n-butanol, and the filtrates were combined. The temperature was controlled at 50° C.-80° C. The filter cake was dried under reduced pressure at a degree of vacuum over 0.08 MPa, and the dried product was added with 7.7 g of liquid alkali (concentrated sodium hydroxide solution with a mass concentration of about 50%) and 160 g of water, stirred and dissolved, 10 g of toluene was added to the water layer for extraction twice, 80 ml of dichloromethane was added to the water layer, the layer was cooled to 10° C.-15° C., and 7.5% hydrochloric acid was added dropwise to adjust the pH to 3-4, the system was kept at 10° C.-15° C. for 1 hour, then cooled to 0° C.-5° C. and kept for 1 hour. The reaction system was filtered, and the filter cake was washed with 20 ml of dichloromethane and 40 g of water respectively, and dried under reduced pressure to obtain 19.7 g of losartan with a yield of 89%. Azide ions (HPIC detection) were not detected (detection limit: 0.081 ppm).

Example 3 Preparation of Losartan 40 g of toluene was added into a four-necked flask, added with 20 g of compound 4, 10.3 g of sodium azide and 18 g of triethylamine hydrochloride under slow stirring. After feeding, the temperature was raised to 90° C.-95° C., and kept for 35 hours-45 hours. After the reaction was completed, 40 g of water was added, and the temperature was reduced to 60° C.-70° C. The reaction system was stood for layering to separate the intermediate layer liquid, 40 ml of n-butanol was added for dissolution, washed twice with 20 g of saturated sodium chloride aqueous solution, 2.0 g of triphenylphosphine and 0.8 g of activated carbon were added, the system was stirred, warmed up to 50° C.-60° C., and de-colored for 2 hours. The reaction system was subjected to hot filtering, and then the filter cake was washed with 10 ml of n-butanol, and the filtrates were combined. The temperature was controlled at 50° C.-80° C. The filter cake was dried under reduced pressure at a degree of vacuum over 0.08 MPa, and the dried product was added with 7.7 g of liquid alkali (concentrated sodium hydroxide solution with a mass concentration of about 50%) and 160 g of water, stirred and dissolved, 10 g of toluene was added to the water layer for extraction twice, 80 ml of dichloromethane was added to the water layer, the system was cooled to 10° C.-15° C., and 7.5% hydrochloric acid was added to adjust the pH to 3-4, the system was kept at 10° C.-15° C. for 1 hour, then cooled to 0° C. to 5° C. and kept for 1 hour. The reaction system was filtered, and the filter cake was washed with 20 ml of dichloromethane and 40 g of water respectively, and dried under reduced pressure to obtain 19.5 g of losartan with a yield of 88%. Azide ions (HPIC detection) were not detected (detection limit: 0.081 ppm).

INDUSTRIAL APPLICABILITY

It can be seen from Examples 1 to 3 that the losartan prepared by the preparation method of the present invention has high yield and high azide removal rate, and no new impurities will be introduced. Since sodium nitrite is not used, the formation of genotoxic impurities nitrosamines is fundamentally eliminated. In addition, the diluent, triphenylphosphine and other reagents used in the preparation method of the present invention have low cost, small consumption, mild operating conditions and good safety, and are suitable for large-scale industrial production.

Unless otherwise specified, the terms used in the present invention have the meanings commonly understood by those skilled in the art.

The described embodiments of the present invention are for exemplary purposes only, and are not intended to limit the scope of protection of the present invention. Those skilled in the art can make various other substitutions, changes and improvements within the scope of the present invention. Therefore, the present invention is not limited to the above embodiments, but only limited by the claims.

The invention claimed is:

1. A preparation method of losartan, wherein the losartan is prepared by reacting a cyano group-containing intermediate represented by formula (I) with an azide reagent in toluene in the presence of a catalyst, wherein, after the reaction is completed, azide ions are removed by means of the following process: adding water to divide the reaction system into three layers, separating the intermediate layer and adding n-butanol to the intermediate layer for dilution, and adding triphenylphosphine to the resulting diluted solution so as to remove residual azide ions from the diluted solution,

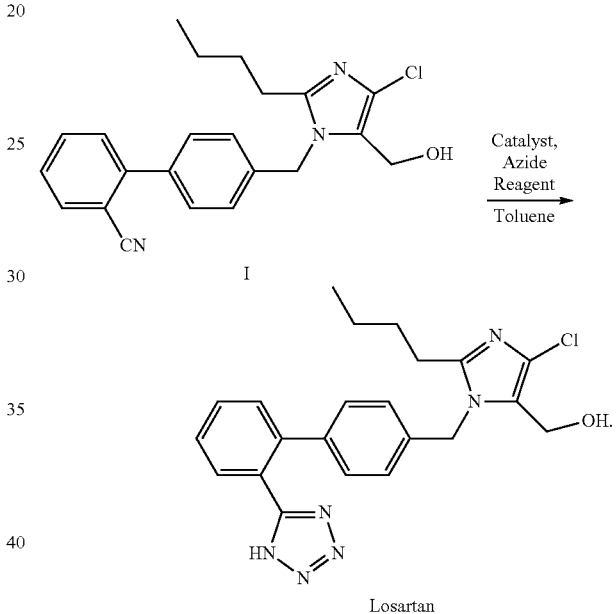

2. The preparation method according to claim 1, wherein the water is added in an amount that is 0.8 times-1.2 times that of the toluene by volume.

3. The preparation method according to claim 1, wherein the triphenylphosphine is added in an amount that is 2%-10% of the cyano group-containing intermediate by mole percentage.

4. The preparation method according to claim 1, wherein the preparation method further comprises adding triphenylphosphine into the diluted solution and simultaneously adding activated carbon for decolorization.

5. The preparation method according to claim 1, wherein the preparation method, after the azide ions are removed, further comprises the following process: evaporating the resulting diluted solution to dryness, adding an alkaline solution for saponification reaction, washing off impurities with toluene, adding a dispersing solvent and adding an acidic solution for acidification, and precipitating crystals to obtain the losartan.

6. The preparation method according to claim 5, wherein the alkaline solution is sodium hydroxide or potassium hydroxide solution with a mass percentage of 1%-5%; and the acidic solution is hydrochloric acid or sulfuric acid solution with a volume percentage of 5%-10%, and is acidified to a pH value of 3-4.

7. The preparation method according to claim 5, wherein the dispersing solvent is dichloromethane.

8. The preparation method according to claim 1, wherein the azide reagent is sodium azide; and the catalyst is triethylamine hydrochloride.

9. The preparation method according to claim 1, wherein a molar ratio of the cyano group-containing intermediate: the azide reagent: the catalyst is 1:2.5-3.5:2.0-3.0.

10. The preparation method according to claim 1, wherein a mass ratio of the cyano group-containing intermediate to the toluene is 1:1-5.

11. The preparation method according to claim 10, wherein a mass ratio of the cyano group-containing intermediate to the toluene is 1:2.

12. The preparation method according to claim 2, wherein the triphenylphosphine is added in an amount that is 2%-10% of the cyano group-containing intermediate by mole percentage.

13. The preparation method according to claim 2, wherein the preparation method further comprises adding triphenylphosphine into the diluted solution and simultaneously adding activated carbon for decolorization.

14. The preparation method according to claim 3, wherein the preparation method further comprises adding triphenylphosphine into the diluted solution and simultaneously adding activated carbon for decolorization.

15. The preparation method according to claim 2, wherein the preparation method, after the azide ions are removed, further comprises the following process: evaporating the resulting diluted solution to dryness, adding an alkaline solution for saponification reaction, washing off impurities with toluene, adding a dispersing solvent and adding an acidic solution for acidification, and precipitating crystals to obtain the losartan.

16. The preparation method according to claim 3, wherein the preparation method, after the azide ions are removed, further comprises the following process: evaporating the resulting diluted solution to dryness, adding an alkaline solution for saponification reaction, washing off impurities with toluene, adding a dispersing solvent and adding an acidic solution for acidification, and precipitating crystals to obtain the losartan.

17. The preparation method according to claim 4, wherein the preparation method, after the azide ions are removed, further comprises the following process: evaporating the resulting diluted solution to dryness, adding an alkaline solution for saponification reaction, washing off impurities with toluene, adding a dispersing solvent and adding an acidic solution for acidification, and precipitating crystals to obtain the losartan.

18. The preparation method according to claim 2, wherein the azide reagent is sodium azide; and the catalyst is triethylamine hydrochloride.

19. The preparation method according to claim 2, wherein a molar ratio of the cyano group-containing intermediate: the azide reagent: the catalyst is 1:2.5-3.5:2.0-3.0.

20. The preparation method according to claim 2, wherein a mass ratio of the cyano group-containing intermediate to the toluene is 1:1-5.

* * * * *